United States Patent [19]

Lillford et al.

[11] Patent Number: 6,090,917
[45] Date of Patent: Jul. 18, 2000

[54] FROZEN FOOD PRODUCT

[75] Inventors: Peter John Lillford; Andrew John McArthur; Christopher Michael Sidebottom, all of Colworth, United Kingdom

[73] Assignee: Good Humor-Breyers Ice Creams, Green Bay, Wis.

[21] Appl. No.: 08/890,489

[22] Filed: Jul. 9, 1997

[30] Foreign Application Priority Data

Jul. 26, 1996 [EP] European Pat. Off. .............. 96305497

[51] Int. Cl.⁷ .............................. A61K 38/00; C07K 5/00; C07K 7/00; A23G 1/22
[52] U.S. Cl. ......................... 530/350; 530/300; 530/326; 530/327; 530/328; 426/100; 426/101; 426/104; 426/139; 426/565
[58] Field of Search .................................... 426/565, 100, 426/101, 104, 139, 656, 660, 521, 524; 530/350, 300, 344, 326, 328

[56] References Cited

U.S. PATENT DOCUMENTS 5,118,792  6/1992  Warren et al. ........................... 530/350

FOREIGN PATENT DOCUMENTS

| 90/13571 | 11/1990 | WIPO . | |
| 92/22581 | 12/1992 | WIPO . | |
| 9222581 | 12/1992 | WIPO ............................ | C07K 15/10 |
| 94/03617 | 2/1994 | WIPO . | |
| 94/11586 | 4/1996 | WIPO . | |

OTHER PUBLICATIONS

European Report dated Mar. 10, 1997.
Hincha Dk et al, Plant Physiology, (1992), 140, 236–240, as cited on p. 2 of the Specification.
Volger et al, Biochimica et Biophysica Acta, 412, (1975), 335–349, "Cryoprotective Leaf Proteins".
Boothe et al, Plant Physiology (1995), 108, 795–803, "Expressionofa low–temperature–inducedprotein in brassica–napus".
Neven et al, Plant Molecular Biology, (1993), 21 (2), 291–305, "Characterizationofa spinach gene responsive to low temperature and water stress".
Salzman et al, vol. 44, No. 4, (1993), "Cold acclimated buds of Vitis spp. express boiling–stable polypeptides analogous to fish antifreeze proteins".
Lin et al, Plant Physiology (1992) 99, 519–525, "DNA sequence analysis of a complimentary DNA for cold–regulated arabidopsis gene COR and characterizationofthe COR 15 polypeptide".
Houde et al, The Plant Journal (1995), 8 (4), 583–593, "Immunolocalizationoffreezing–tolerance–associated proteins in the cytoplasm and nucleoplasm of wheat crown tissue".
Lin c, Biochemical and Biophysical Research Communications, (1992), vol. 183, No. 3, A cold–regulatedArabidopsis gene encodes a polypeptide having potents cryoprotective activity.

*Primary Examiner*—Avis M. Davenport
*Attorney, Agent, or Firm*—James J. Farrell

[57] ABSTRACT

A process for the recovery of AFPs from natural sources, said process involving the steps of a) isolating an AFP containing juice from the natural source;

b) heat treating the natural source or the AFP containing juice to a temperature of at least 60° C.;

c) removing the insoluble fraction.

2 Claims, No Drawings

FROZEN FOOD PRODUCT

TECHNICAL FIELD OF THE INVENTION

The invention relates to a process for the isolation of anti-freeze proteins (AFPs) and frozen food product containing AFPs.

BACKGROUND TO THE INVENTION

Anti-freeze proteins (AFPs) have been suggested for improving the freezing tolerance of foodstuffs.

For the purpose of the invention, the term AFP has the meaning as well-known in the art, namely those proteins which exhibit the activity of inhibit the growth of ice crystals. See for example U.S. Pat. No. 5,118,792.

WO 90/13571 discloses antifreeze peptides produced chemically or by recombinant DNA techniques. The AFPs can suitably be used in food-products. Example 3B shows modified ice crystal shapes if a water-ice mixture is frozen into a film in combination with 0.01 wt % of AFP.

WO 92/22581 discloses AFPs from plants which can be used for controlling ice crystal shape in ice-cream. This document also describes a process for extracting a polypeptide composition from extracellular spaces of plants by infiltrating leaves with an extraction medium without rupturing the plants.

WO 94/03617 discloses the production of AFPs from yeast and their possible use in ice-cream. WO 96/11586 describes fish AFPs produced by microbes.

Several literature places also mention the isolation and/or use of plant proteins for cryoprotection. Cryoprotective proteins have a function in the protection of plant membranes against frost damage. These proteins, however, do not possess recrystallisation inhibition properties and are, therefore, not embraced within the terms AFPs.

Hincha in Journal of Plant Physiology, 1992, 140, 236–240 describes the isolation of cryoprotective proteins from cabbage.

Volger in Biochimica et Biiophysica Acta, 412 (1975), 335–349 describes the isolation of cryoprotective leaf proteins from spinach.

Boothe in Plant Physiol (1995), 108: 759–803 describes the isolation of proteins from *Brassica napus*. Again, these proteins are believed to be cryoprotective proteins rather than AFPs.

Neven in Plant Molecular Biology 21: 291–305, 1993 describes the DNA characterisation of a spinach cryoprotective protein.

Salzman in Abstracts and Reviews of the 18th Annual Meeting of the ASEV/Eastern Section in Am. J. Enol. Vitic., Vol. 44, No. 4, 1993 describes the presence of boiling-stable polypeptides in buds of Vitis. Although the proteins are analogous to fish antifreeze peptides, they are cryoprotective proteins and not AFPs.

Lin in Biochemical and Biophysical Research Communication, Vol. 183, No. 3, 1992, pages 1103–1108 and in Lin, Plant Physiology (1992) 99, 519–525 describes the 15 kDa cryoprotective polypeptide from *Arabidopsis Hakaira*.

Houde in The Plant Journal (1995) 8(4), 583–593 mentions cryoprotective proteins from wheat.

Furthermore—as illustrated in example VIII—extracts of cabbage, spinach, *Brassica napus* and Arabidopsis do not have recrystallisation inhibition proteins after heating.

Up till now, however the use of AFPs has not been applied to commercially available food products. One reason for this are the high costs and complicated process for obtaining AFPs. Another reason is that the AFPs which until now have been suggested for use in frozen food products cannot be incorporated in the standard formulation mix, because they tend to destabilise during processing especially during the pasteurisation step. This destabilisation is believed to be caused by the denaturation of the AFPs; this is a well-known effect commonly observed for peptides and proteins.

The present invention aims at providing solutions to these problems.

Surprisingly it has been found that AFPs can be isolated from natural sources such as cold-acclimatised plants by means of a new relatively simple process. This process leads for the first time to the identification of AFPs which can conveniently be incorporated in a mix for the preparation of frozen products before the pasteurisation thereof.

Accordingly in a first aspect, the invention relates to a process for the recovery of AFPs from natural sources, said process involving the steps of a) isolating a AFP containing juice from the natural source;

b) heat treating the natural source or the AFP containing juice to a temperature of at least 60° C.;

c) removing the insoluble fraction.

Step c of the above process will usually take place after steps a and b. Step a and b can be done in any desired order, for example step a followed by step b (in that case the AFP rich juice will be heated) or step b followed by step a (in that case the natural source will be heated) or step a and b simultaneously.

Surprisingly we have found that the isolation process of the invention has a number of advantages.

Firstly by using the process it is no longer necessary to avoid rupturing of the natural source such as plants such as required in the processes according to WO 92/22581. This immediately significantly increases the commercial applicability of the process, for example as compared to WO 92/22581, because high investment costs for specific processing are no longer necessary.

Also by using the high temperatures it seems possible to extract from a large group of peptides present in the natural sources a new selection of very active AFPs from the natural material, said AFPs including peptides which are very active w.r.t. ice-recrystallisation inhibition properties.

Thirdly, contrary to expectations, the use of high temperatures does not denature all the proteinaceous material, but does only seem to denature some of the proteins, while the remaining AFPs have an increased temperature stability. This renders it possible to include the isolated AFPs in compositions which need to be subjected to higher temperatures e.g. a pasteurisation step. This is especially surprising, because for example the AFPs from WO 92/22581 appear not stable under heating conditions (see example VI).

The process of the invention includes in step b the heating of the natural source or the AFP rich juice to a temperature of more than 60° C. Preferably the temperature is from 60 to 110° C., most preferably from 80 to 105° C. The heating step can take place after the isolation of the protein rich juice (step a) or before the isolation of the protein rich juice. Any suitable way to heat the juice can be used, for example conventional or microwave heating, heating optionally with an added extraction medium, steaming etc.

If an extraction medium is used, preferably it is used in small volumes to avoid unnecessary dilution of the AFP fraction. Any suitable extraction medium can be used, although the use of water is especially preferred. If desired, additives may be added to the water prior to using it as an extraction medium. Most preferred, however water substantially free of additives is used.

The process of the invention can be applied to any natural source of heat-stable AFPs. Included in this list are plants, fishes, insects and microorganisms. Both natural occurring species may be used or species which have been obtained through genetic modification. For example microorganisms or plants may be genetically modified to express AFPs and the AFPs may then be isolated in accordance to the present invention. AFPs having at least 80%, more preferred more than 95%, most preferred 100% homology to the AFPs directly obtained from natural sources can thus be obtained. For the purpose of the invention proteins possessing this high level of homology are also embraced within the term AFPs. Also these transformed microorganism or plants capable of expressing genes encoding the AFPs are also embraced within the scope of the invention.

Genetic manipulation techniques may be used to produce the heat stable AFPs described in the invention. An appropriate host cell or organism would be transformed by a gene construct that encodes the desired heat stable polypeptide. The nucleotide sequence coding for the heat stable polypeptide can be inserted into a suitable expression vector containing the necessary elements for transcription and translation and in a manner that they will be expressed under appropriate conditions (eg in proper orientation and correct reading frame and with appropriate targeting and expression sequences). The methods required to construct these expression vectors are well known to those skilled in the art.

A number of expression systems may be utilised to express the heat stable polypeptide coding sequence. These include, but are not limited to, bacteria, yeast insect cell systems, plant cell culture systems and plants all transformed with the appropriate expression vectors.

A wide variety of plants and plant cell systems can be transformed with the nucleic acid constructs of the polypeptides isolated in the heat stable extract. Preferred embodiments would include, but are not limited to, maize, tomato, tobacco, carrots, strawberries, rape seed and sugar beet.

Preferably the AFP is derived from plants (this means that either the AFP is directly obtained from the plant as natural source or AFPs having a high degree of homology to these AFPs are transgenetically produced in other organisms). Any plant containing heat stable AFPs can be used, preferably however are naturally occurring plants (or their genetic modified versions) which are able to grow under cold conditions such that they contain AFPs. Especially preferred is the use of winter-rye, perennial grasses and sedges. Other suitable plants may for example come from the group of woody plants, winter-cereals etc.

Especially preferably the heat stable AFPs are derived from *Acer saccharoides,* Bamboo, Buddleia, *Isothecium myosuroides, Ramalina farinaceae, Usnea subfloridana,* Forsythia, Oxalis, *Poa Trivialis, Lolium Perenne, Holcus Lanatus, Bromus Sterilis, Parodiochloa flabellata, Deschampsia antartica, Carex aquatilis, Colobanthus quintensis* and *Agrostis tenuis, Festuca contracta* and *Poa annua*.

The AFP rich juice can be separated from its source by any convenient process for example pressing, filtering, homogenising, extraction etc. Preferably the natural source of AFP such as the plant material is made into small pieces or into a slurry before the protein rich fraction is collected, for example by filtering. This maceration can be done by any suitable method, for example in a blender. It will be well within the ability of the skilled person to divide the material into such a form that collection of the protein rich juice can readily take place.

After collecting and heating (in the desired order) the protein fraction the resulting AFP containing sample can then be treated by any convenient process in order to remove the insoluble fraction and retain the AFP rich liquid fraction. The insoluble fraction can be removed e.g. by filtering, precipitation etc. The AFP rich liquid can then advantageously be further processed to concentrate or isolate the AFPs to bring them in a form suitable for further use. Examples of suitable processes are drying to obtain a powder or paste, further concentration to obtain an AFP concentrate, chromatography to separate the AFPs from the extraction medium etc. Again it will be well within the ability of the skilled person to determine the suitable means and conditions for appropriate isolation.

For some natural sources the AFPs obtained by the above methods may consist of a mixture of two or more different AFPs. If desired these AFPs can be separated by any conventional process for example chromatography or other processes based on the differences in physical/chemical properties such as molecular weight.

Also if desired the amino acid composition and sequence of the isolated AFPs can be determined. Any suitable method for determining these can be used. Examples of suitable methods are described in the examples. Also if desired the nucleic acid sequence that encodes the AFPs can be determined. Vector containing a nucleic acid sequence capable of encoding the amino acids are also embraced within the scope of the invention.

Based on the above information it is also possible to genetically modify other natural sources such that they produce the advantageous AFPs as identified hereabove. Examples of suitable AFPs are described in the examples.

It has been found that the AFPs obtained by the above process have an increased ability to withstand thermal treatment. It is believed that such AFPs have never before been isolated. As described above this increased thermal resistance is particularly of interest for use in food-products which undergo a heating step, for example pasteurisation.

Accordingly another aspect of the invention relates to AFPs which have a thermal stability as evidenced by no significant reduction in the recrystallisation inhibition properties after heat-treatment for one hour at 80° C. or 10 minutes at 100° C. A suitable test for determining the ice recrystallisation inhibition properties is described in the examples and involves the quick freezing to −40° C. followed by storage for one hour at −6° C. Preferably AFPs which are subject to this test after heat-treatment result in an ice crystal particle size which is less than 5 $\mu$m larger than the ice crystal size of a sample with the same AFP which was not heat-treated. Preferably the difference is less than 3 $\mu$m, most preferred less than 1 $\mu$m.

Preferably those AFPs are chosen which have significant ice-recrystallisation inhibition properties. A suitable test for determining the recrystallisation inhibition properties is indicated in the example VI. Preferably AFPs in accordance to the invention provide a ice particle size following an ice recrystallisation inhibition assay—as described in the examples—of 15 $\mu$M or less, more preferred from 5 to 15 $\mu$m.

The AFPs can conveniently be used in food products, preferably in food products which are frozen or intended to be frozen. Especially preferred is the use of AFPs in products which are heated e.g. by pasteurisation or sterilisation prior to freezing. Especially preferred is the use in frozen confectionery products.

Examples of such food products are: frozen confectionery mixes such as ice-cream mixes and water-ice mixes which are intended to be pasteurised prior to freezing. Such mixes are usually stored at ambient temperature. Suitable product forms are for example: a powder mix which is packed for example in a bag or in sachets. Said mix being capable of forming the basis of the frozen food product e.g. after addition of water and optionally other ingredients and—optional—aeration.

Another example of a suitable mix could be a liquid mix (optionally aerated) which, if necessary after addition of further components and optional further aeration can be frozen.

The clear advantage of the above mentioned mixes is that the presence of the AFP ingredient makes that the mixes can be frozen under quiescent conditions, for example in a shop or home freezer without the formation of unacceptable ice crystal shapes and hence with a texture different to products normally obtained via quiescent freezing.

Very conveniently these mixes are packed in closed containers (e.g. cartons, bags, boxes, plastic containers etc). For single portions the pack size will generally be from 10 to 1000 g. For multiple portions pack sizes of up to 500 kg may be suitable. Generally the pack size will be from 10 g to 5000 g.

As indicated above the preferred products wherein the AFPs are used are frozen confectionery product such as ice-cream or water-ice. Preferably the level of AFPs is from 0.0001 to 0.5 wt % based on the final product. If dry-mixes or concentrates are used, the concentration may be higher in order to ensure that the level in the final frozen product is within the above ranges.

Surprisingly it has been found that compositions of the invention can contain very low amounts of AFPs while still being of good quality.

Surprisingly it has been found that the level of AFPs can be as low as 0.1 to 50 ppm while still providing adequate recrystallisation properties and temperature tolerance in frozen confectionery products. Although applicants do by no means wish to be bound by any theory, the reason for this may be that the interaction between the solids of the frozen confectionery and the AFPs provides an excellent mechanism for inhibiting crystal growth. Most conveniently the level of AFP is from 1 to 40 ppm, especially preferred from 2 to 10 ppm.

For the purpose of the invention the term frozen confectionery product includes milk containing frozen confections such as ice-cream, frozen yoghurt, sherbet, sorbet, ice milk and frozen custard, water-ices, granitas and frozen fruit purees. For some applications the use in fermented food products is less preferred.

Preferably a the level of solids in the frozen confection (e.g. sugar, fat, flavouring etc) is more than 4 wt %, for example more than 30 wt %, more preferred from 40 to 70 wt %.

Frozen confectionery products according to the invention can be produced by any method suitable for the production of frozen confectionery. Especially preferably however all the ingredients of the formulation are fully mixed before pasteurisation and before the freezing process starts. The freezing process may advantageously involve a hardening step, for example to a temperature of −30 Fahrenheit or lower.

EXAMPLE I

Isolation of AFPs by first collecting the juice followed by heat treatment and isolation of the AFP.

Winter rye (Halo variety) was cut in January (mean temperature in that month was 3.5° C. ensuring the appropriate cold acclimatization of the plants). The tissue was rapidly transported into the laboratory for further handling and washed thoroughly with water to remove dirt.

400 g of the clippings were homogenised at ambient temperature in a Waring blender with 800 g water until the leaf tissue was completely disrupted. The AFP rich juice was collected by filtering through 4 layers of muslin.

The AFP rich juice was then subjected to a temperature treatment by boiling the juice for 10 minutes. This caused the precipitation of protein while the AFP for use in accordance to the invention remained in solution. The supernatant was separated from the precipitate by centrifuging at 15,000 g for 20 minutes or by further filtration through muslin.

The AFPs can be isolated from the supernatant by freeze drying.

For control purposes an apoplastic extract (extracellular extract) of winter rye can be obtained as follows: The leaves from 30 days cold acclimated rye plants were cut into 3 cm lengths and thoroughly washed in distilled water to remove any cell contents. The leaf pieces were patted dry on paper towel and totally immersed in an extraction medium of 5 mM EDTA, 10 mM ascorbic acid, 2 mM caproic acid, 2 mM benzamidine and 1 mM Phenylmethylsulphonyl Fluoride (PMSF). They were then vacuum infiltrated in a Buchner flask for 60 minutes after which time the leaves were removed and patted completely dry. They were then arranged lengthways is a cut off plastic syringe barrel and centrifuged gently at 2000×g for 30 minutes. The apoplastic extract was collected in an eppendorf tube below the syringe.

EXAMPLE II

Isolation of AFPs by first heating the natural source, followed by isolating the AFP rich juice and isolation of the AFP.

Mixed grass tissue (*Poa Trivialis, Lolium Perenne, Holcus Lanatus, Bromus Sterilis*) was cut in January (mean temperature in that month was 3.5° C. ensuring the appropriate cold acclimatization of the plants). The grass tissue was rapidly transported into the laboratory for further handling and washed thoroughly with water to remove dirt.

500 g of grass clippings was placed in a 650 Watt microwave oven and heated at full power for 5 minutes, whereby the temperature was raised to 85 to 100° C. The grass clippings were then cooled to ambient temperature.

Alternatively the grass clippings are mixed with 500 g boiling water and the mixture is re-heated to 100° C. followed by boiling for 10 minutes under stirring and then allowed to cool to 60° C.

After the heating step the AFP rich juice was separated from the clippings by filtering. The mass was stirred continuously for 5 minutes in the presence of an equal volume of water and then squeezed through 3 layers of muslin.

The supernatant can be freeze dried to remove the water followed by storage. Alternatively the supernatant can be frozen for storage.

EXAMPLE III

A liquid pre-mix for preparing ice-cream was made by mixing:

| Ingredient | % by weight |
| --- | --- |
| Skimmed milk powder | 11.390 |
| Sucrose | 3.410 |
| Maltodextrine (MD40) | 4.000 |
| Locust bean gum | 0.072 |
| Corn Syrup 63DE | 20.705 |
| Guar Gum | 0.048 |
| Genulacta L100 | 0.020 |
| Butter | 9.015 |
| Avicel RC581 | 0.240 |
| Gelatin | 0.140 |
| Monoglyceride (palmitate) | 0.450 |
| Vanillin | 0.010 |
| AFP (of example I*) | 0.100 or none (control) |
| Water | balance |

*Note: AFP is added as concentrated AFP solution using some of the added water as a diluent, percentage refers to amount of AFP.

This mix can conveniently be pasteurised at 85° C. for 15 seconds and stored chilled in a can.

The mixes can be used in the preparation of a ice-cream by whipping with a conventional house-hold mixer to an overrun of about 100%, followed by quiescently freezing into a house-hold freezer. The composition according to the invention had a markedly better texture than the control sample.

Very good results are obtained by using the AFP of Example II instead of the AFP of example I.

EXAMPLE IV

A liquid premix for the preparation of ice-cream was prepared by mixing:

| Ingredient | % by weight |
| --- | --- |
| Skimmed milk powder | 10.00 |
| sucrose | 13.00 |
| maltodextrine (MD40) | 4.00 |
| Locust bean gum | 0.14 |
| butter oil | 8.00 |
| monoglyceride (palmitate) | 0.30 |
| vanillin | 0.01 |
| AFP (of example I*) | 0.01 or none (control) |
| water | balance |

*Note: AFP is added as concentrated AFP solution in some of the water, percentage refers to amount of AFP.

The ingredients were mixed at ambient temperature followed by pasteurisation for 60 seconds at 89° C. The mix was aseptically filled into packs of 500 ml, sealed and stored at ambient temperatures.

The mix can be used for the preparation of ice-cream by whipping it with a conventional house-hold mixer to an overrun of about 70% followed by freezing under quiescent conditions in a house-hold freezer.

After two months storage the composition according to the invention had a markedly better texture than the control sample.

Very good results are obtained by using the AFP of Example II instead of the AFP of example I.

EXAMPLE V

Example IV was repeated, but now the ice-cream mix was pre-aerated to an overrun of 70% prior to aseptically filling and sealing.

The resulting product can be stored at ambient temperature and an ice-cream can be produced by placing the mix in a house-hold freezer and freezing under quiescent conditions.

EXAMPLE VI

The ice recrystallisation inhibition properties of the AFPs can determined as follows:

A sample of an AFP containing product was adjusted to a sucrose level of 30 wt % (If the starting level of the sample was more than 30% this was done by dilution, if the starting level was lower sucrose was added to the 30% level).

A 3 μL drop of the sample was placed on a 22 mm coverslip. A 16 mm diameter cover-slip was then placed on top and a 200 g weight was placed on the sample to ensure a uniform slide thickness. The edges of the coverslip were sealed with clear nail varnish.

The slide was placed on a Linkham THM 600 temperature controlled microscope stage. the stage was cooled rapidly (50° C. per minute) to −40° C. to produce a large population of small crystals. The stage temperature was then raised rapidly (50° C. per minute) to −6° C. and held at this temperature.

The ice-phase was observed at −6° C. using a Leica Aristoplan microscope. Polarised light conditions in conjunction with a lambda plate were used to enhance the contrast of the ice crystals. The state of the ice phase (size of ice crystals) was recorded by 35 mm photomicrography at T=0 and T=1 hour.

Generally this test can be applied to any suitable composition comprising AFP and water. Generally the level of AFP in such a test composition is not very critical and can for example be from 0.0001 to 0.5 wt %, more preferred 0.0005 to 0.1 wt %, most preferred 0.001 to 0.05 wt %, for example 0.01 wt %.

Any suitable composition comprising AFP and water can be used to carry out the test. Generally, however, it will not be necessary to obtain the AFP in purified form. For practical applications normally it would suffice to prepare a liquid extract or juice of natural material, wherein this extract or juice can then be tested.

This method can be applied for example to the AFP containing extracts as obtained in example I or II, with or without a concentration step.

The recrystallisation inhibition properties of several samples was measured. The samples were obtained from rye which were harvested at several moments during the year. The AFP juices obtained after extraction and heating in accordance to example I were measured for their recrystallisation properties as above. As a comparison rye was used which was grown in a greenhouse (at temperatures which normally do not induce AFP formation)

The following ice crystal sizes were measured

| Sample | Ice crystal size after 1 hour (μm) |
| --- | --- |
| Control | 25 |
| sample December | 17 |
| sample January | 10 |
| sample February | 15 |
| sample March | 18 |

-continued

| Sample | Ice crystal size after 1 hour ($\mu$m) |
|---|---|
| sample April | 18 |
| sample May | 25 |

These measurements show that for good AFP activity the plants should be harvested during the winter months e.g. December–April. Especially preferred are samples capable of providing ice crystal sizes of 15 $\mu$m or less. In this case this can be achieved by harvesting the plants in January or February.

The same measurements were done on the AFP samples of January which were heat treated (1 hour at 60° C.). No significant reduction in recrystallisation properties was observed.

As a comparison the apoplastic extract of example I was used. This resulted in a final ice crystal size after 1 hour of 11.1 $\mu$m; after heat treatment by boiling for 10 minutes at 100° C. the test resulted after 1 hour in a ice crystal size of 16.8 $\mu$m. This example shows that the apoplastic extract from winter rye is not heat stable.

EXAMPLE VII

Non heat treated grass extract from grass harvested in January was obtained from Silsoe (UK). The extract was centrifuged for 1 hour to remove soil and insoluble debris as follows, Centrifuge:Sorvall RC3C, Rotor:H6000A, Temperature:+5° C., Rotor Speed:5000 rpm(7268 g).

A sample of the extract was freeze dried to determine its total solids content. This was found to be 11.48 mg/ml. The dried extract was then rehydrated with 30% Sucrose solution to its original total solids concentration. Several solutions were prepared by diluting the extract as necessary with 30% Sucrose solution.

Antifreeze activity was measured using the assay of example VI.

The T=0 and T=1 hour pictures from the recrystallisation inhibition assays had their mean ice crystal sizes measured using the Zeiss TGA 10 analyser. The results obtained are shown in the table below.

| Sample | Total Solids (mg/ml) | Ice Crystal Size ($\mu$m) T = 0 | Ice Crystal Size ($\mu$m) T = 1 hour at −6° C. | Ice Crystal Growth in 1 hour at −6° C. ($\mu$m) |
|---|---|---|---|---|
| Undiluted | 11.48 | 5.2 | 7.3 | 2.1 |
| 50% Extract | 5.74 | 5.5 | 7.6 | 2.1 |
| 25% Extract | 2.87 | 6.3 | 8.9 | 2.6 |
| 12.5% Extract | 1.435 | 6.6 | 13.1 | 6.5 |
| 6.25% Extract | 0.7175 | 8.1 | 14.7 | 6.6 |
| 3.125% Extract | 0.359 | 7.4 | 17.0 | 9.6 |
| 1.5625% Extract | 0.179 | 9.0 | 20.3 | 11.3 |

These results show the variation in final crystal size and the change in ice crystal size over 1 hour at −6° C. for the various dilutions of grass extract. It can be seen that the solids level in the grass extract can be varied in a wide range while still good recrystallisation inhibition properties are obtained. Preferably those concentrations are chosen which result in an ice crystal size after 1 hour of 15 micrometer or less.

A similar test was done with grass extract which had been subjected to heat treatment (10 minutes at 100° C.). No significant deterioration of recrystallisation inhibition properties was seen.

Additionally the grass extracts of example II were tested using the same recrystallisation inhibition test. The following results were obtained:

| Heat treatment | Crystal Size in $\mu$m | |
|---|---|---|
| | T = 0 | T = 1 |
| 60° C. 1 hour | 9.6 | 11.1 |
| Boil 10 minutes | 9.8 | 11.3 |

These results show that even after heating the extract of cold acclimatised grass maintained the ability to inhibit ice crystal growth.

EXAMPLE VIII

Several AFP containing plants were harvested in January. Extracts were obtained by grounding fresh tissue, for example roots, stems, buds or leaves with a pestle and mortar (cooled to 4° C.) in a equal volume of buffer A (10 mM EDTA, 20 mM Ascorbic acid, buffered with Tris to pH 7.4) held on ice. The homogenates are filtered through one or more layers of muslin and kept on ice prior to further used.

The extracts were subjected to the recrystallisation inhibition test of example VI both after heating for 60 C. for 1 hour and boiling for 10 minutes.

The following plants contained heat stable AFPs as evidenced by the maintenance of recrystallisation inhibition properties: *Acer saccharoides,* Bamboo, Buddleia, *Isothecium myosuroides, Ramalina farinaceae, Usnea subfloridana,* Forsythia, Oxalis, *Poa Trivialis, Lolium Perenne, Holcus Lanatus, Bromus Sterilis, Parodiochloa flabellata, Deschampsia antartica, Carex aquatilis, Colobanthus quintensis* and *Agrostis tenuis, Festuca contracta* and *Poa annua.*

The following plants did not contain heat stable AFPs: cabbage, spinach, *Brassica napus* and Arabinopsis.

EXAMPLE IX

The thermal hysteresis activity of the AFPs can be tested as follows:

1 ml samples were placed in Eppendorfs in a hot water bath and heated for 1 hour at 60° C. The thermal hysteresis properties of the sample were then measured as follows:

The melted product is placed on a microslide (Camlab Cambridge, path length 0.1 mm). The ends of the microslide are sealed with petroleum jelly.

Ice is introduced into the sample using an aerosol freezing spray. The slide was then immersed in ethanol temperature regulated bath at −0.1° C. After 5 minute equilibration the sample is checked. if the ice melts completely the temperature of the bath was lowered in 0.1° C. steps followed by equilibration. These steps are repeated until a temperature was reached where a small amount of ice crystals exist in the sample. After equilibration at that temperature, the bath temperature was decreased in steps of 0.01° C. per minute. The freezing point of the sample is recorded as the temperature at which the ice propagation begins from the equilibrated crystals.

The melting temperature of the sample is then determined by raising the temperature starting at the freezing point in steps of 0.01° C. per minute until all ice crystals melt. This temperature is the melting temperature of the sample.

The thermal hysteresis of the sample is the difference between the melting temperature and the freezing temperature.

This test procedure is done on a first sample (prior to heat treatment) and on a second sample after heat treatment, followed by cooling.

Similarly the heat stability can be determined by the above test wherein the sample is boiled in water for 30 seconds followed by determining the thermal hysteresis. The thermal hysteresis of several samples was measured.

The samples were obtained from winter-rye which were harvested at several moments during the year. The AFP juices obtained after extraction and heating in accordance to example I were measured for their thermal hysteresis as in example VI. As a comparison winter-rye was used which was grown in a greenhouse (at temperatures which normally do not induce AFP formation)

The following thermal hysteresis was measured

| Sample | Thermal hysteresis (° C.) |
|---|---|
| Control | 0.04 |
| sample December | 0.18 |
| sample January | 0.21 |
| sample February | 0.17 |
| sample March | 0.15 |
| sample April | 0.12 |
| sample May | 0.05 |

These measurements show that for good AFP activity the plants should be harvested during the winter months e.g. December–March.

The same measurements were done on the AFP samples of January which were heat treated (1 hour at 60° C.) No significant reduction in thermal hysteresis was observed.

EXAMPLE X

Determination of amino acid sequence of AFPs

The heat stable grass extract of example II was concentrated approximately ten times using an Amicon ultrafiltration chamber with 10 kDa cut-off membrane. The resulting concentrate was loaded onto a Mono Q (Pharmacia) HR 5/5 FPLC anion exchange column. Binding to the column was in 50 mM Tris/HCl buffer pH 8.5 and the RI active fraction was eluted with a linear gradient of NaCl to a final concentration of 0.5M in the same pH 8.5 Tris buffer. Chromatography was carried out at a flow rate of 1 ml min$^{-1}$ and 1 ml fractions were collected and assayed for recrystallisation inhibition activity (as in example IX).

The active fractions were pooled together and concentrated to a volume of 0.05 ml on a centricon PM10 centrifugal concentrator (Amicon) centrifuged at 10,000 rpm for 10 minutes in a Sorvall SS 34 rotor (8×50 ml). The concentrate was loaded onto a Superdex 75 PC 3.2/30 gel filtration column running on a SMART microseparation system (Pharmacia). The column was eluted with 50 mM Tris/HCl buffer pH 8.5 at a flow rate of 0.05 ml min$^{-1}$. Fractions of 0.05 ml were collected after the sample was loaded to a total volume of 3.5 ml. Fractions were assayed for recrystallisation inhibition activity (as in example IX) and the most active fractions were subjected to separation on an SDS PAGE gel and electroblotting prior to N-terminal sequencing.

The active Superdex 75 fractions were taken up in gel loading buffer (50 mM Tris/HCl, pH 6.8, 10% glycerol, 10 mM dithiothreitol, 2% SDS) and then separated on a 10% polyacrylamide gel following the Laemmli method. After electrophoresis the gel was sandwiched against a sheet of methanol wetted Problott (Perkin Elmer) membrane and electroblotted at 20 volts for 16 hours in 10 mM 3(cyclohexylamino)-1-propane sulphonic acid (CAPS) buffer (pH 11.0) containing 10% methanol. After blotting, the membrane was washed briefly with methanol and then milli Q (Millipore) water and the bound proteins visualised with a solution of 0.1% (w/v) coomassie brilliant blue.

Two protein bands of apparent molecular weights 25 kDa and 35 kDa were visualised by the coomassie staining. The 35 kDa protein appeared to particularly closely correlate to the most RI active fractions. Both of these bands were excised with a scalpel blade and sequenced. An unstained area of the membrane corresponding to an apparent molecular weight of 65–75 kDa was also subjected to sequencing as silver staining of gels of the most active fractions had previously shown a protein band at this molecular weight.

All three excised areas of membrane were sequenced by loading into a Blott sequencing cartridge and the sequence determined using reaction and conversion cycles as described by the manufacturer (Perkin-Elmer). N-terminal sequence-listings are given below.

The 25 kDa AFP comprises a sequence from the N terminus substantially homologous to:

ALA-THR-ILE-THR-ALA-VAL-ALA-VAL-LEU-LYS-X-THR-VAL-GLU-VAL-X-ILE-VAL-PRO-THR   (SEQ ID NO:1)

The 35 kDa AFP comprises a sequence from the N terminus substantially homologous to:

ALA-GLN-PHE-THR-ILE-THR-ASN-LYS-CYS-GLN-PHE-THR-VAL-TRP-ALA-ALA-X-VAL-PRO   (SEQ ID NO:2)

The 65–70 kDa AFP comprises a sequence from the N terminus substantially homologous to:

X-GLU-GLN-PRO-ASN-THR-ILE-X-GLY-THR   (SEQ ID NO:3)

In each sequence X denotes an unknown which may be any amino acid found in plant proteins. For the purpose of the invention the term substantially homologous refers to at least 80% overlap in amino acids, more preferred more than 90%, most preferred 95 to 100%.

We claim:

1. A process for the recovery of AFPs from natural sources, said process involving the steps of a) isolating an AFP containing juice from the natural source;

b) heat treating the natural source or the AFP containing juice to a temperature of at least 60° C.;

c) removing the insoluble fraction.

2. A process in accordance to claim 1, wherein steps a and b (in either order) take place before step c.

* * * * *

SEQUENCE LISTING

<160> NUMBER OF SEQ ID NOS: 3

<210> SEQ ID NO 1
<211> LENGTH: 20
<212> TYPE: PRT
<213> ORGANISM: MIXED GRASS
<220> FEATURE:
<221> NAME/KEY: UNSURE
<222> LOCATION: (11)..(16)
<223> OTHER INFORMATION: Xaa represents any amino acid found in plant
      protein

<400> SEQUENCE: 1

Ala Thr Ile Thr Ala Val Ala Val Leu Lys Xaa Thr Val Glu Val Xaa
 1               5                  10                  15

Ile Val Pro Thr
             20

<210> SEQ ID NO 2
<211> LENGTH: 19
<212> TYPE: PRT
<213> ORGANISM: MIXED GRASS
<220> FEATURE:
<221> NAME/KEY: UNSURE
<222> LOCATION: (17)
<223> OTHER INFORMATION: Xaa represents any amino acid found in plant
      protein

<400> SEQUENCE: 2

Ala Gln Phe Thr Ile Thr Asn Lys Cys Gln Phe Thr Val Trp Ala Ala
 1               5                  10                  15

Xaa Val Pro

<210> SEQ ID NO 3
<211> LENGTH: 10
<212> TYPE: PRT
<213> ORGANISM: MIXED GRASS
<220> FEATURE:
<221> NAME/KEY: UNSURE
<222> LOCATION: (1)..(8)
<223> OTHER INFORMATION: Xaa represents any amino acid found in plant
      protein

<400> SEQUENCE: 3

Xaa Glu Gln Pro Asn Thr Ile Xaa Gly Thr
 1               5                  10